Figure 1:
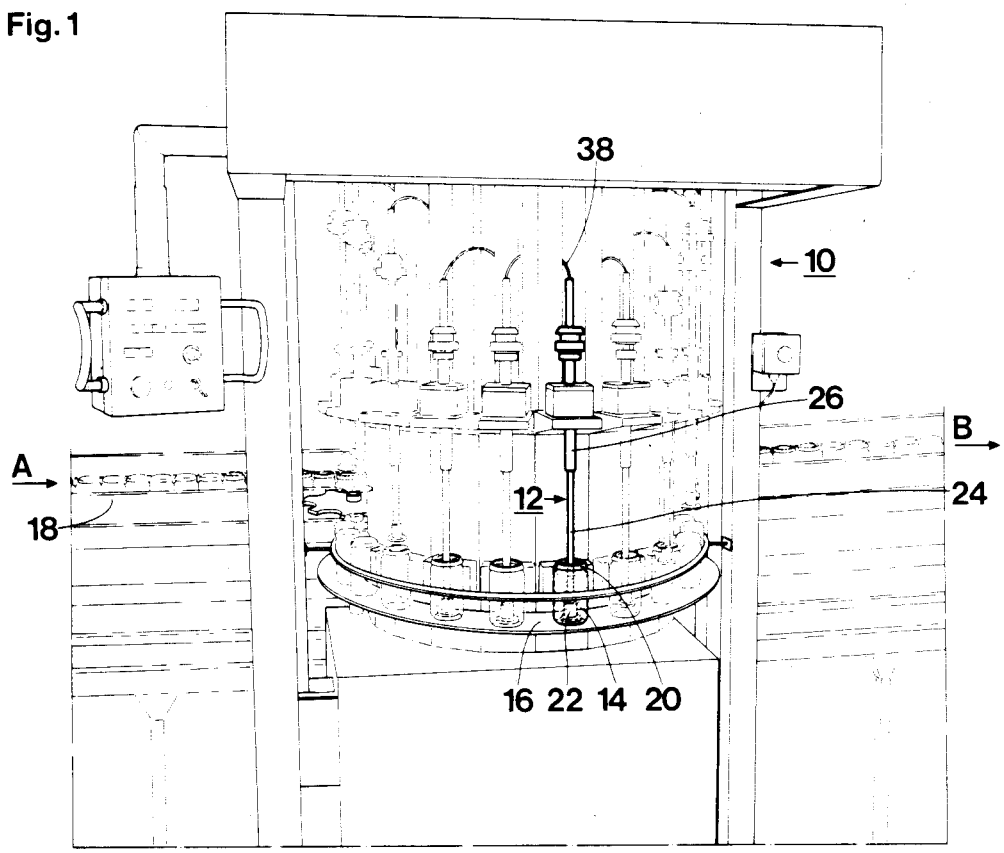

United States Patent [19]

Bogatzki

[11] Patent Number: 4,798,096
[45] Date of Patent: Jan. 17, 1989

[54] APPARATUS FOR CHECKING HOLLOW GLASS CONTAINERS

[75] Inventor: Hans-Ulrich Bogatzki, Zürich, Switzerland

[73] Assignee: Elpatronic AG, Switzerland

[21] Appl. No.: 94,686

[22] Filed: Sep. 9, 1987

[30] Foreign Application Priority Data

Oct. 10, 1986 [CH] Switzerland .................. 04054/86

[51] Int. Cl.⁴ .............................................. G01N 3/08
[52] U.S. Cl. ............................................ 73/12; 209/530
[58] Field of Search ............... 73/865, 8, 12; 209/523, 209/552, 530, 531, 522, 597, 600, 601, 604, 934; 198/339.1, 340; 65/158; 364/552

[56] References Cited

U.S. PATENT DOCUMENTS

| 2,352,091 | 6/1944 | Fedorchak et al. | 209/601 |
| 3,355,811 | 12/1967 | Tailleur | 209/531 |
| 3,955,408 | 5/1976 | Northup | 73/812 |
| 4,593,369 | 6/1986 | Thompson | 364/552 |

FOREIGN PATENT DOCUMENTS

| 2410110 | 3/1974 | Fed. Rep. of Germany . |
| 2437759 | 8/1974 | Fed. Rep. of Germany . |
| 2308910 | 2/1975 | Fed. Rep. of Germany . |
| 2545678 | 10/1975 | Fed. Rep. of Germany . |
| 2635519 | 8/1976 | Fed. Rep. of Germany . |
| 2648076 | 10/1976 | Fed. Rep. of Germany . |

Primary Examiner—Jerry W. Myracle
Assistant Examiner—Robert R. Raevis
Attorney, Agent, or Firm—McCormick, Paulding & Huber

[57] ABSTRACT

The apparatus comprises a sensor element (22) which is fitted into a rod (24) which is movable backwards and forwards and by means of which it can be moved in the interior of a hollow glass container (14) to within the vicinity of the bottom. The sensor element is provided with a movably suspended plate (30) at the bottom. If the plate (30) comes into contact with an obstacle in the form of a glass filament (bird swing or spike) in the interior of the container, it is deflected and actuates a proximity switch which delivers a signal by means of which an ejection device is actuated. The apparatus serves, in particular, for the checking of wide-necked containers in which defects in the form of spikes are considerably more frequent than defects in the form of bird swings.

2 Claims, 3 Drawing Sheets

APPARATUS FOR CHECKING HOLLOW GLASS CONTAINERS

The invention relates to an apparatus for checking hollow glass containers for defects, particularly in the form of spikes or bird swings, having a sensor element and a switching device which can be actuated by this.

During the manufacture of hollow glass ware on automatic glass processing machines, a feed drip or gob of the molten glass is introduced out of the feeder channel of the refiner into the gathering mould and pressed therein by means of a plunger whereupon the so-called parison is transferred into the finishing mould by tipping through 180°, finish-blown and ejected. If the glass does not have the optimum temperature during the pressing operation or if the plunger is badly lubricated, the plunger may pull a filament out of the parison when travelling outwards, namely from the inner surface of the parison wall or of the bottom of the of the parison. This filament breaks off at the "sticking point" on the plunger and remains in the interior of the parison. During the finish blowing, a filament originating from the bottom is blown downwards and may retain its shape as a result of which a spike remains behind in the finished hollow glass container. The filament may, however, also join the inner wall of the parison laterally even while in the gathering mould. A filament originating from this inner wall will likewise bear against the inner wall. During the finish blowing, a so-called bird swing (also known as a chicken roost or a bird cage) then forms. Such bird swings usually occur in the lower third of the hollow glass container. Such spikes and bird swings occur more frequently in wide-necked containers than in bottles, for example, with a narrow mouth. It is true that defects of this kind only occur once in 100,000 hollow glass containers as regards order of magnitude and are therefore not frequently defects, but hollow glass containers with such defects must be discarded under all circumstances if they are intended to be filled with foods. Actually, when such hollow glass containers are filled with non-liquid filling material (yoghurt, baby food, coffee powder, etc) spikes and bird swings frequently break off and remain in the filling material. They may likewise break off if the filling material is stirred with a spoon or the like before consumption, which applies in particular to wide-necked containers.

If a defect of the said type, that is to say a spike or a bird swing is found during the manufacture of hollow glass containers in the glassworks, five pallets, for example, of finished hollow glass containers before and after it are blocked and all the hollow glass containers are sorted by hand because it can always be assumed that such defects do not occur in isolation but accumulate once they occur. In order to achieve the highest possible production rates, the hottest possible glass is used in the glassworks, but then "plunger sticking" causing such defects also occurs more easily because the plunger lubrication is more frequently impaired by hotter glass. Apart from the above-mentioned danger during consumption, therefore, such defects lead to the further disadvantage that they can have a considerable adverse effect on the production rates in the glassworks.

In the prior art, there are therefore already apparatuses for checking hollow glass containers for such defects but so far as is known they all work with optical examination. Such a known apparatus of the type given in the preamble to patent claim 1 (DE-OS No. 26 35 519) serves to establish the presence of defects on the inner bottom surface of hollow glass containers, particularly in the form of cracks, bodies foreign to the glass, melted or sintered glass or similar deficiencies. For this purpose, a plurality of light sources are arranged so that they illuminate the inner surface of the bottom of the glass container uniformly, through the side wall of the container. In the absence of bodies foreign to the glass or the like, substantially all the light is reflected by the inner surface of the bottom. If bodies foreign to the glass are present, the light falling on these is reflected and conveyed through the bottom surface to a light-sensing element which then actuates a switching or reject device so that the glass container in question is discarded as a reject.

It is a disadvantage of this known checking apparatus that, at the most, spikes of considerable size can be detected, and that bird swings or other fine glass filaments on the inner wall of the glass container, that is to say not on the bottom, cannot be detected at all. The container wall actually usually comprises mould seam marks which produce strong signals during optical scanning. Furthermore, the bottom of the container usually carries bosses from the bottom of the gathering mould which likewise produce strong signals. A thin spike at a corresponding point will produce a much weaker signal than the bosses from the bottom of the gathering mould. Furthermore, banana-shaped marks ("knurling") on the outside of the bottom produce very strong signals. Writing patterns on the container wall, near the bottom, also produce strong signals which mask those of a spike or a bird swing. With such an optical apparatus, therefore, it is very difficult to distinguish between normal optical defects, that is to say those to which there is no objection, and real defects. The consequence is that the sensitivity of the optical examination has to be adjusted so that even many hollow glass containers which are actually usable, are discarded. A filament which bears closely against the wall is difficult to detect optically. The filament can be detected at the point where it emerges from the glass because it is thicker there. This produces a signal but mould seam marks, air bubbles in the glass and the like produce a similar signal. If the sensitivity of the optical checking is adjusted so that it does not detect the mould seam marking, then it would not detect a bird swing either.

It is true that a further known apparatus for checking glass containers (DE-AS No. 24 37 759) works with a mechanical sensing element which, when it bends, closes an indicating circuit through an electrical contact, but only defects in the edge, that is to say in the sealing surface of the container, can be detected with this apparatus, namely in the form of air bubbles which have opened in the edge surface of the container.

Furthermore, apparatuses are known for the automatic checking of hollow glass containers (DE-PS No. 23 08 910) and DE-AS No. 25 45 678) but they likewise work with optical systems which illuminate the bottom through the mouth of the hollow glass container and therefore have similar disadvantages to the known optical examination apparatus first mentioned. In addition, there are already also checking apparatuses working with high frequency or capacitively (DE-PS Nos. 26 48 076) or 24 10 110), with which liquid residues can admittedly be detected in hollow glass containers but not defects of the type here in question such as spikes and bird swings. With the exception of the known optical examination device first mentioned, all the further known checking apparatuses mentioned are also intended primarily for checking hollow glass containers when they are re-used but not for checking hollow glass containers when they are produced in the glass works.

It is the object of the invention to develop an apparatus particularly suited to detect defects in glass containers in the form of spikes or bird swings, without requiring that the hollow glass containers be discarded as a result of the checking.

According to the invention, this problem is solved in that the sensor element is fitted to a rod which can be moved backwards and forwards and by means of which it can be moved in the interior of the container down to the vicinity of the bottom, and the sensor element comprises, at the side remote from the rod, a pressure member which actuates the switching device on touching an obstacle.

In the apparatus according to the invention, the pressure member is, on the one hand so sensitive that it actuates the switching device on the touching an obstacle and, on the other hand, so robust that it breaks an obstacle such as a bird swing or a spike for example. If the glass container is turned over after checking and possibly additionally blown out, the broken filament falls out of the container. Thus the apparatus offers the advantage over optical apparatuses that it not only detects defects of the said type but also eliminates these at the same time. This does not have to be so, however, since the control of the apparatus may also be adjusted so that, on touching an obstacle, the rod is immediately withdrawn and an ejection device is actuated so that the hollow glass container is ejected as a reject. With the apparatus according to the invention, if the rod has been moved into a predetermined distance from the bottom of the container without the pressure member having come into contact with an obstacle, the hollow glass container has passed the test and is considered usable. Hollow glass containers discarded as faulty as a result of pronounced optical irregularities therein cannot occur with the apparatus according to the invention because, if the sensor element has been moved close to the bottom without contact with an obstacle having occurred, the switching device is not actuated in any case. This is of particular importance in the case of wide-necked containers for the checking of which the apparatus is provided in particular, because in these, defects of the type in question here are particularly disadvantageous and the apparatus according to the invention does not cause any reduction of the production capacity in the glass works during their checking.

It is true that the apparatus can easily be used also at the filling site but work is usually carried on there with a filling speed which exceeds the checking speed of the apparatus according to the invention (300-400 hollow glass containers/hour) by a multiple. The apparatus according to the invention is not only in a position to detect defects reliably and also to eliminate these in addition and to prevent erroneous results during the checking, but also it has a robust construction and is simple to service. The pressure member may be any robust part which is in a position to break an obstacle, particularly spikes or bird swings and to actuate the switching device on this contact with the obstacle. The signalling of the pressure member for the switching device may be effected purely mechanically or piezo-electrically if the pressure member consists of piezoelectric material which generates an electrical signal for the actuation of the switching device under the action of pressure.

Advantageous developments of the invention form the subject of the sub-claims.

In the development of the invention according to claim 2, the pressure member is simply a plate which is mounted for easy movement and which, on touching an obstacle, approaches the proximity switch and actuates this as a result. In general, any proximity sensor can be used as a proximity switch which can be actuated, by way of example, inductively, capacitively or by means of a light barrier, and in the last-mentioned case, the light barrier would be interrupted by the plate.

The sleeve and the plate articulately secured thereto form an interchangeable set which is selected according to the internal diameter of the mouth of the hollow glass container to be checked and which can be easily locked on the holder, for example by means of a ball, prestressed by a spring, on the holder, which ball engages in a corresponding opening in the sleeve. In each interchangeable set, the sleeve is the same; it simply carries a plate with a different diameter. Hollow glass containers with a twist-off closure only occur in a few sizes in a standard series so that the whole range of sizes of wide-necked containers for example can be covered with a few interchangeable sets.

The side of the plate remote from the rod is at substantially the same distance from the inside of the bottom at all points when it is at the predetermined proximity to the bottom.

The predetermined distance may be about 2 mm for example. All defects, for example in the form of spikes, which are within this tolerance range of 2 mm, are negligible. Hollow glass containers, the bottom of which is thicker than normal by at least 2 mm would, of course, be discarded. This should be regarded as a disadvantage because a bottom differing from the usual thickness indicates a fault in the glass processing machine.

The plate, like the sleeve, consists of light material because the sensor element should not be too heavy since, in the usual case of the rod which can be moved backwards and forwards vertically, it hangs on this which in turn is constructed in the form of a telescope.

The plate made of plastics material is armoured with spring steel so that spikes cannot bore into it. The only thing which is important is that the plate is light and carries a hard covering on its side remote from the rod.

The joint has a particularly simple construction.

The proximity switches are actuated simultaneously if the switching device should touch down on the bottom of the container. Otherwise, usually only one proximity switch of the switching device is actuated at a time, if the plate touches an obstacle.

The apparatus enables a distinction to be made between body defects, which are detected above the bottom of the container, and bottom defects are detected on the bottom itself. It is an advantage to be able to keep these two types of defect apart because as a result conclusion can be drawn as to the nature of the fault which has led to the causing of the defect found during the checking, during the shaping operation. If the switching device is actuated by the plate, this is first recorded in the evaluation logic which then actuates the ejection device and the signal indicating device. The evaluation logic also records the region in which the defect has appeared in order to establish whether the actuation of the switching device has been caused by a bird swing on the inner wall of the hollow glass container or by a spike thereof, in order to establish further how frequently faults occur etc. If bird swings occur, for example, the frequency of these can be evaluated electronically. Thus it is possible to determine by which mould the bird swings have been produced. A mould number reader can then be actuated so that subsequently all the hollow glass containers which originate from the mould in question are ejected.

Finally, a particular advantage of the apparatus according to the invention is to be seen in every embodiment thereof, in that with it, an apparatus for stress testing glass containers arranged hanging, which forms the subject of the same applicant's pending patent application Ser. No. 57,489, filed June 3, 1987, can be changed over, in a simple manner, from stress testing to the checking of glass containers. Actually, the impacting rod of the stress testing apparatus merely has to be replaced by the rod with the sensor element fitted thereto and the apparatus has to be adjusted so that the sensor element does not touch down on the bottom of the container but is only moved in the vicinity of the bottom. The investment costs called for by the invention can therefore be kept low. In addition, hollow glass containers can either be subjected to a stress test or checked for defects selectively with the same apparatus by simple changing over.

One example of embodiment of the invention is described in more detail below with reference to the drawings.

Figure 2:
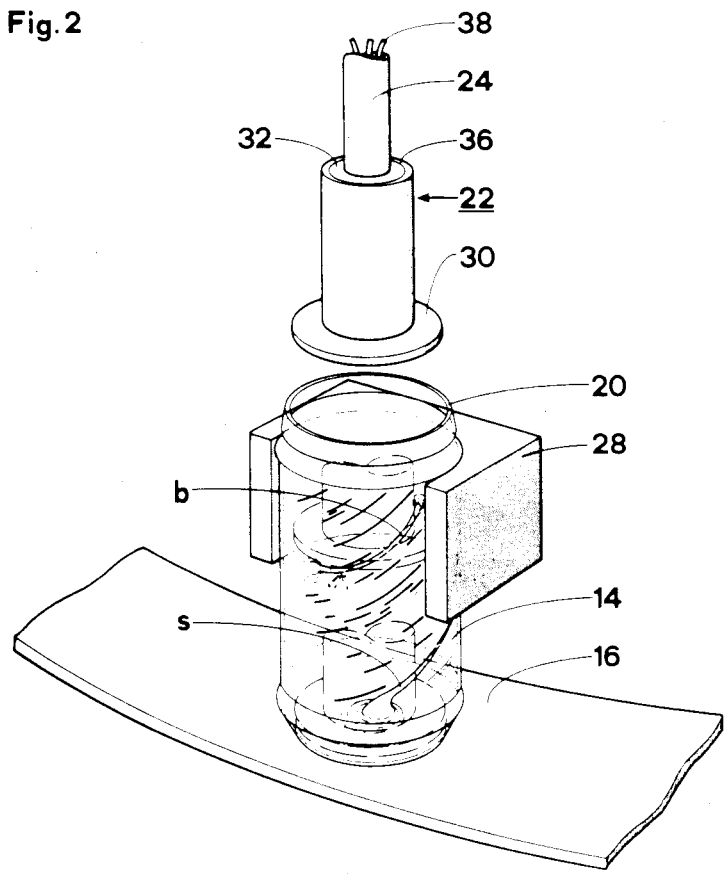
Figure 3:
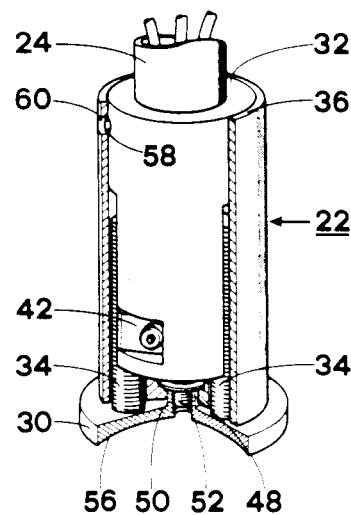
Figure 4:
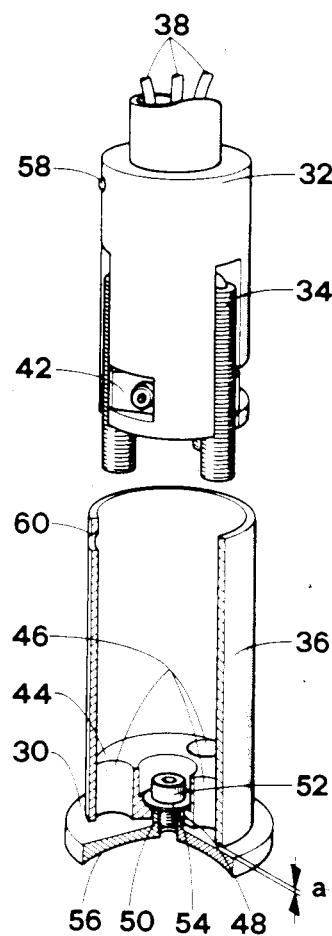
Figure 5:
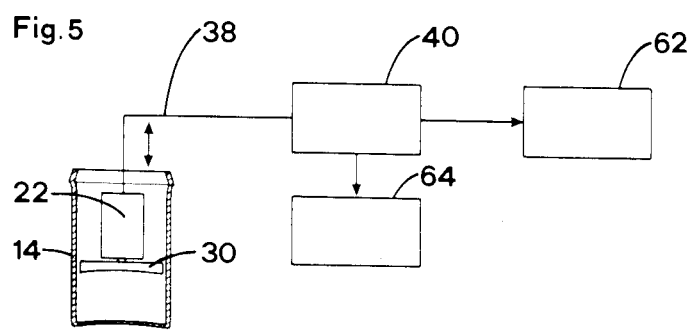

FIG. 1 shows the test turntable of a machine having a plurality of apparatuses according to the invention, FIG. 2 shows the sensor element of the apparatus according to the invention in several phases during the checking of a hollow glass container, FIG. 3 shows a partial longitudinal sectional view of the sensor element of the apparatus according to the invention, FIG. 4 shows the sensor element of FIG. 3 in an exploded illustration and FIG. 5 shows a very simplified block circuit diagram of the apparatus according to the invention.

FIG. 1 shows a test turntable 10 of a machine for checking hollow glass containers which is provided with a plurality of checking apparatuses 12. Apart from the checking apparatuses 12, the test turntable 10 may have substantially the same construction as the test turntable in the stress testing apparatus described in the pending patent application Ser. No. 57,489, filed June 3, 1987. The only difference is that there impacting rods are set down on the bottom of the container each time whereas here checking apparatuses 12 are used, the sensor element of which is merely brought into the vicinity of the bottom, and that during the checking, the hollow glass containers 14 are not arranged hanging but each stand on a rotary table 16. The hollow glass containers 14 are conveyed by a conveyor 18 in the direction of the arrow A to the test turntable 10 into which they run on the left in FIG. 1. On the right in FIG. 1, the hollow glass containers 14 leave the test turntable 10 and are conveyed further in the direction of the arrow B by the conveyer 18. The test turntable 10 could be followed by an inverting device, not illustrated, which turns each hollow glass container 14 with its mouth 20 downwards so that any foreign bodies which may be present can fall out of the hollow glass container. At the same time, the hollow glass containers may additionally be blown out.

According to the illustration of FIGS. 1 and 2, each checking apparatus 12 comprises a sensor element 22 which is secured to a rod 24 which can be moved backwards and forwards vertically. The rod 24 is guided in a tube 26. Each checking apparatus 12 is arranged centrally above a receiving device 28 each of which receives a hollow glass container 14 from the above 18. Disposed adjacent to the circular path of the receiving devices 28 is a curved track, not visible in FIG. 1, on which carriages, likewise not illustrated, run to each of which one of the rods 24 is adjustably secured. In FIG. 1, it can be seen that, in the test turntable rotating in clockwise direction, the rods 24 move in their tubes 26, according to the course of the invisible curved track, downwards from the top left towards the middle and then upwards again towards the right. Each rod 24 is secured to its carriage so that a pressure member 30, provided on the sensor element 22 at the bottom, is about 2 mm above the bottom of the hollow glass container at the end of the downward movement of the rod, unless there is an obstacle with a height exceeding 2 mm on the bottom. When the rods move increasingly downwards from left to right in FIG. 1, the rods 24 with the sensor elements 22 are introduced into the mouths 20 and moved downwards until the said distance of 2 mm is reached. The the rods move upwards again in the course of which they pull the sensor elements out of the hollow glass containers 14. If, up to the said approach to the bottom of the container, the pressure member 30 has not come into contact with any obstacle, the checked hollow glass container counts as good, otherwise it is ejected as a reject, which is described in more detail below.

FIG. 2 shows a wide-necked container as an example of a hollow glass container 14 to be checked. In the example of embodiment described here, the pressure member 30 of the sensor element 22 is an easily movable plate. The diameter of the plate 30 is selected so that it can just be introduced readily into the mouth 20 of the hollow glass container 14. According to the illustration in FIG. 2, there are two defects in the form of glass filaments in the hollow glass container 14, the upper glass filament b being a so-called bird swing, that is to say a glass filament which extends from a point on the inner wall of the container, through the interior of the container, to another point on the inner wall of the container, and the lower glass filament s being a so-called spike, that is to say a glass filament which extends upwards from the bottom of the container. The sensor element 22 is illustrated in three phases, namely firstly above the container mouth 20 before introduction into the interior of the container, secondly in the interior of the container when touching an obstacle in the form of the upper glass filament b and thirdly in a lowest position near the bottom.

According to the illustration in FIGS. 3 and 4, the sensor element 22 consists of a holder 32 which is secured to the rod 24 and in which three proximity switches 34 are detachably secured, and of a sleeve 36 with the plate 30. Conductors 38, which establish the connection between the sensor element 22, a current source not illustrated and an evaluation logic 40 illustrated in FIG. 5, are provided in the rod 24. The proximity switches 34 used as a switching device for the checking apparatus 12 in the example of embodiment described here are standard components available commercially. Each switch 34 includes an outer cylindrical capsule that has a lower end face for sensing movement of the pressure plate toward it. The proximity switches 34 are arranged symmetrically round the longitudinal axis of the holder 32 and are each adjustably secured to the holder by means of a clip 42. The holder 32 consists of light material (for example plastics material, aluminium or the like) and is cylindrical in construction.

The sleeve 36 is likewise cylindrical in construction and may consist of the same material as the holder 32. The sleeve 36 comprises a bottom wall 44 which is provided with three bores 46 for the proximity switches 34 projecting out of the holder 32 at the bottom and also with a central bore 48. The plate 30 is provided, at its top, with a central stud 50 which comprises a tapped bore into which a screw 52 is screwed. Disposed between the head of the screw 52 and the stud 50 is a washer 54 with which the plate is supported round the central bore. The stud 50 has adequate clearance in the central bore 48 and the height of the stud as far as the underside of the washer 54 is selected so that the top of the plate is at a distance a of about 0.5 mm from the bottom of the bottom wall 44. In this manner, the plate 30 is suspended for easy movement on the sleeve 36 by means of a joint which consists of the stud 50, the washer 52, the screw 52 and the central bore 48. The distance a remains unaltered so long as the plate 30 does not come into contact with an obstacle such as a glass filament of the type shown in FIG. 2 for example. The lower end faces of the proximity switches 34 are flush with the underside of the bottom wall 44 so that the spacing a also exists between the plate 30 and the proximity switches 34. This flush adjustment of the proximity switches 34 can easily be brought about by means of the clips 42. The sleeve 36 with the plate 30 is pushed onto the holder 32 until a ball 58, preloaded by a spring, on the holder snaps into a corresponding opening 60 in the sleeve 36 and so detachably locks the sleeve to the holder. In this locked position, the lower end faces of the proximity switches 34 are flush with the underside of the bottom wall 44. The bore 46 have a somewhat larger diameter than the proximity switches 34 so that the latter do not hamper the pushing of the sleeve 36 onto the holder 32.

The sleeve 36 and the plate 30 form a set which is exchanged for another set if hollow glass containers are to be checked, the mouth 20 of which has a different internal diameter. The diameter of the plate of each set is selected so that the plate just fits through the mouth 20 so that as large an area as possible of the interior of the container can be covered by the plate. In FIG. 5, the region below the mouth 20 of a wide-necked container which cannot be covered by the plate is indicated by hatching. Since bird swings normally project beyond the hatched region into the interior of the container, they can also be reached by the plunger 30.

The side of the plate 30 remote from the rod 24 has a concave curvature matching the convex arching of the bottom of the hollow glass container 14 to be checked so that the above mentioned distance of 2 mm, which the plate has in the vicinity of the bottom in the example of embodiment described here, is present everywhere between plate and bottom. The plate likewise consists of light material, for example plastic material, and is provided at its side remote from the rod 24, with a hard covering 56, for example of spring steel, so that spikes or other pointed foreign bodies cannot damage the plate.

The apparatus described above for checking hollow glass containers works as follows:

The sensor element 22 is moved vertically into the interior of the hollow glass container 14 in the manner described above. If, in the course of this, the plate comes into contact with an obstacle such as the upper glass filament b FIG. 2, it is deflected upwards towards the sleeve 36 and actuates at least one of the proximity switches 34. Since, in the example of embodiment described here, the rod 24 continues its downward movement, the said glass filament is broken off by the plate. If, during its further downward movement, the plate comes into contact with the lower glass filament s in FIG. 2, at least one of the proximity switches is again actuated and this glass filament is also broken off. If the test turntable is followed by an inverting device, as mentioned, the broken-off glass filaments later fall out of the hollow glass container 14. If there is no defect in the form of an obstacle to the plate 30 in the hollow glass container 14, the plate moves as far as the height of 2 mm above the bottom and then back again without one of the proximity switches 34 having been actuated. This hollow glass container is regarded as good whereas every other hollow glass container in which at least one of the proximity switches has been caused to respond is regarded as a reject.

As the plate 30 approaching at least one of the proximity switches a signal is provided to the evaluation logic 40 via the conductors 38. The evaluation logic then delivers a corresponding signal to an ejection device 64 so that this is actuated when the hollow glass container 14, which has caused the signal, arrives at the ejection device 64 which may be located at the exit from the test turntable. Using the signals delivered by the proximity switches 34 the evaluation logic 40 also records the region of the interior of the container in which the defect is which has caused the signal, in order to establish whether the signal has been triggered by a bird swing on the inner wall of the container or by a spike. A signal indicating device 62 connected there to then indicates what type the defect was. If bird swings occur as defects, their frequency can be evaluated. Thus it can be found by which mould the bird swings are being produced.

The checking apparatus 12 could also be controlled in such a manner that the sensor element is moved back immediately as soon as the plate 30 comes into contact with as obstacle. This would involve greater expenditure on control, however. It is therefore simpler to destroy defects with the sensor element and always to move the sensor element to within the vicinity of the bottom of the hollow glass container 14. If the thickness of the bottom should exceed the usual value by more than 2 mm in the present example of embodiment, the sensor element will obviously come to rest on the bottom so that the plate actuates all three proximity switches 34 and this hollow glass container is also ejected as a reject. It is true that the thicker bottom does not represent a "dangerous" defect but it indicates that the mould in question is possibly not working correctly. The corresponding type of signal also indicated by the signal indicating device 62 is that action can be taken at the corresponding mould.

I claim:

1. An inspection apparatus for large mouth glass containers comprising:
a sensing device movable toward and away from the interior bottom wall of a glass container to be inspected, said device including a housing and a support rod for the housing, means for moving the support rod to position the housing inside a glass container at an inspection position, said device including a pressure plate movably mounted to said housing for limited movement toward and away from said housing, said housing including at least one proximity switch having a sensing face to detect movement of said plate from a normal position towards said housing at least when said device is in its inspection position, said inspection position for said housing and said normal position for said plate providing a positive test for a glass container, said plate movement toward said housing being caused by contact between said plate and a defect in a glass container being inspected, said housing including a sleeve member, a bottom wall for the sleeve member, said proximity switch secured in the bottom wall of the sleeve member so that its sensing face is provided in generally co-planar relationship with the lower face of the sleeve bottom, said pressure plate having a lower face that this contoured to correspond closely to the convex contour of a satisfactory glass container bottom wall to be inspected, said pressure plate provided with a central opening to receive a threaded screw, said screw being received loosely in a bore provided for it in the bottom wall of said housing sleeve, said screw having a head adapted to engage a shoulder on the sleeve bottom to define a normal displacement between the sleeve bottom and the upper surface of the plate.

2. The apparatus of claim 1 above wherein said pressure plate is fabricated from a light weight material with a thin shell defining a lower face, said thin shell material being of harder consistency then that of the glass being inspected.

* * * * *